United States Patent
Fishman

(10) Patent No.: US 9,549,943 B2
(45) Date of Patent: Jan. 24, 2017

(54) A3 ADENOSINE RECEPTOR LIGANDS FOR USE IN TREATMENT OF A SEXUAL DYSFUNCTION

(71) Applicant: CAN-FITE BIOPHARMA LTD., Petach Tikva (IL)

(72) Inventor: Pnina Fishman, Herzliya (IL)

(73) Assignee: CAN-FITE BIOPHARMA LTD., Petach Tikva (IL)

( * ) Notice: Subject to any disclaimer, the term of this patent is extended or adjusted under 35 U.S.C. 154(b) by 0 days.

(21) Appl. No.: 14/420,439

(22) PCT Filed: Aug. 8, 2013

(86) PCT No.: PCT/IL2013/050675
§ 371 (c)(1),
(2) Date: Feb. 9, 2015

(87) PCT Pub. No.: WO2014/024195
PCT Pub. Date: Feb. 13, 2014

(65) Prior Publication Data
US 2015/0216889 A1    Aug. 6, 2015

(30) Foreign Application Priority Data

Aug. 9, 2012 (IL) .......................................... 221382
Nov. 12, 2012 (IL) .......................................... 222988

(51) Int. Cl.
*A61K 31/4745* (2006.01)
*A61K 31/7076* (2006.01)

(52) U.S. Cl.
CPC ....... *A61K 31/7076* (2013.01); *A61K 31/4745* (2013.01)

(58) Field of Classification Search
None
See application file for complete search history.

(56) References Cited

U.S. PATENT DOCUMENTS

| | | |
|---|---|---|
| 5,443,836 A | 8/1995 | Downey et al. |
| 5,573,772 A | 11/1996 | Downey et al. |
| 5,688,774 A | 11/1997 | Jacobson et al. |
| 5,773,423 A | 6/1998 | Jacobson et al. |
| 6,048,865 A | 4/2000 | Baraldi |
| 6,664,397 B1 | 12/2003 | Fletcher et al. |
| 6,987,129 B2 | 1/2006 | Mak et al. |
| 2003/0143282 A1* | 7/2003 | Fishman ............ A61K 38/1709 424/548 |
| 2007/0179175 A1 | 8/2007 | Lunn |
| 2009/0054476 A1 | 2/2009 | Goblyos et al. |
| 2010/0254965 A1* | 10/2010 | Xia .................... A61K 49/0004 424/94.6 |

FOREIGN PATENT DOCUMENTS

| | | |
|---|---|---|
| WO | 9502604 A1 | 1/1995 |
| WO | 9727173 A2 | 7/1997 |
| WO | 9920284 A1 | 4/1999 |
| WO | 9906053 A1 | 11/1999 |
| WO | 0119360 A2 | 3/2001 |
| WO | 02055085 A2 | 7/2002 |
| WO | 2004086034 A2 | 7/2004 |
| WO | 2007045989 A1 | 4/2007 |
| WO | 9006089 A2 | 1/2009 |

OTHER PUBLICATIONS

Wen, Arterioscler Thromb Vasc Biol. 2012;32:845-850.*
Mayor, BMJ vol. 328, Mar. 6, 2008.*
Gerbino, "Remington: the science and practice of pharmacy" 21st edition Publisher: Lippincott Williams & Wilkins, American Journal of Pharmaceutical Education (2005).
Gao et al "2-Substituted adenosine derivatives: affinity ad efficacy at four subtypes of human adenosine receptors" Science Direct, Biochemical Pharmacology. 68 :1985-1993 (2004).
Chiang et al "Adenosine modulation of neurotransmission in penile erection" J clin Pharmac 38: 357-362 (1994).
Gao et al "Selective Allosteric Enhancement of Agonist Binding and Function at Human A3 Adenosine Receptors by a Series of Imidazoquinoline Derivatives" Molcular Pharmacology, American Society. 62 (1) 81-89 (2002).
Fishman et al "Pharmacology and Therapeutic Applications of A3 Receptor Subtypes" 3: 463-469 (2003).
Liu et al., Chronic Administration of Sildenafil Modified the Impaired VEGF System and Improved the Erectile Function in Rats with Diabetic Erectile Dysfunction, J Sex Med, 7:3868-3878 (2010).

* cited by examiner

*Primary Examiner* — Layla Berry
(74) *Attorney, Agent, or Firm* — Browdy and Neimark, PLLC

(57) ABSTRACT

The present disclosure provides an $A_3$ adenosine receptor ($A_3AR$) ligand for the treatment of sexual dysfunction. In some embodiments the $A_3AR$ ligand is selected from an $A_3AR$ agonist and $A_3AR$ allosteric enhancer. The present disclosure also provides a method a method and pharmaceutical composition for treating a sexual dysfunction, the method comprises administering to a subject having the sexual dysfunction an amount of an $A_3$ adenosine receptor ($A_3AR$) ligand. In some embodiments, the $A_3AR$ ligand is an $A_3AR$ agonist and more specifically, IB-MECA.

17 Claims, No Drawings

A3 ADENOSINE RECEPTOR LIGANDS FOR USE IN TREATMENT OF A SEXUAL DYSFUNCTION

TECHNOLOGICAL FIELD

This invention relates to $A_3$ adenosine receptor ligands for use in treatment.

BACKGROUND

Sexual problems are defined as difficulty during any stage (desire, arousal, orgasm, and resolution) of the sexual act, which prevents the individual or couple from enjoying sexual activity. As such, the term "Sexual dysfunction" is understood in the art to cover a wide variety of problems and is generally classified into four categories: sexual desire disorders, sexual arousal disorders, orgasm disorders, and sexual pain disorders.

Sexual dysfunctions are most common in the early adult years, with the majority of people seeking care for such conditions during their late 20s through 30s. The incidence increases again in the perimenopause and postmenopause years in women, and in the geriatric population, typically with gradual onset of symptoms that are associated most commonly with medical causes of sexual dysfunction.

The cause of sexual dysfunction may be psychological, physical or a combination of same. For example, reduced sexual desire (decreased libido) may be caused by a decrease in the normal production of estrogen (in women) or testosterone (in both men and women); aging, fatigue, pregnancy, and medications (e.g. SSRI antidepressants which include fluoxetine (Prozac), sertraline (Zoloft), and paroxetine (Paxil) all known for reducing desire in both men and women), and psychiatric reasons such as depression and anxiety.

Sexual arousal disorders, including erectile dysfunction, in men (referred to in the past as impotence), and any of several specific problems with desire, arousal, or anxiety in women (referred to in the past as frigidity) may be associated with decreased blood flow or lack of vaginal lubrication. Chronic disease may also contribute to these difficulties, as well as the nature of the relationship between partners.

Orgasm disorders (persistent delay or absence of orgasm following a normal sexual excitement phase) may be caused by SSRI antidepressants.

Finally, sexual pain, which affect almost exclusively women include dyspareunia (painful intercourse) and vaginismus (an involuntary spasm of the muscles of the vaginal wall, which interferes with intercourse) and may be caused by physical or psychological parameters.

A variety of treatments are acceptable for sexual dysfunction, starting from antidepressants, if the dysfunction is caused by depression, medical drugs and devices, such as Sildenafil (Viagra), tadalafil (Cialis), and vardenafil (Levitra), vasodilators, implants, hormonal treatment, such as estrogen, nutrition and supplements (e.g. vitamin C, vitamin E), herbs etc.

GENERAL DESCRIPTION

The present disclosure provides, in accordance with a first of its aspects, an $A_3$ adenosine receptor ($A_3AR$) ligand for use in the treatment of sexual dysfunction. The $A_3AR$ ligand may be equally used in female or male subjects and treat a variety of sexual disorders embodied by the term sexual dysfunction, as further detailed below.

The present disclosure also provides, in accordance with a second of its aspects, a method of treating a sexual dysfunction in male and/or female subjects comprising administering to the subject having a sexual dysfunction an $A_3AR$ ligand.

The present disclosure also provides, in accordance with a third of its aspects, a pharmaceutical composition for treating a sexual dysfunction in a subject, the composition comprising a physiologically acceptable carrier and an amount of an $A_3AR$ ligand effective to improve sexual function of said subject.

In one particular embodiment, the $A_3AR$ ligand is an agonist, in particular, $N^6$-(3-iodobenzyl)-adenosine-5'-N-methyluronamide (IB-MECA).

In one another particular embodiment, the $A_3AR$ ligand is an allosteric enhancer of the receptor, in particular, N-(3,4-Dichloro-phenyl)-2-cyclohexyl-1H-imidazo[4,5-c]quinolin-4-amine.

DETAILED DESCRIPTION OF EMBODIMENTS

The present disclosure is based on a phase 3 (randomized, double-masked, placebo-controlled) clinical study involving oral administration of CF101, an experimental pharmaceutical composition where the active ingredient is $N^6$-(3-iodobenzyl)-adenosine-5'-N-methyluronamide (IB-MECA, CF101), to patients with moderate to severe dry eye disease. In the study, some of the patients experienced erection or increase in sexual desire which led to the conclusion that $A_3$ adenosine receptor agonists, such as IB-MECA, are effective agents for treating sexual dysfunction.

The present disclosure is also based on the finding that mice treated with an $A_3AR$ allosteric enhancer, N-(3,4-Dichloro-phenyl)-2-cyclohexyl-1H-imidazo[4,5-c]quinolin-4-amine (LUF6000, CF602), exhibited erection.

Thus, in accordance with a first of its aspects, the present disclosure provides an $A_3AR$ ligand for use in the treatment of a sexual dysfunction.

As appreciated, while the invention is described in the following detailed description with reference to an $A_3AR$ ligand for use in treating a sexual dysfunction, it is to be understood that the present disclosure also encompass uses of $A_3AR$ ligand for treating sexual dysfunction, pharmaceutical compositions comprising the $A_3AR$ ligand for said treatment and methods of treatment of sexual dysfunction making use of the said ligand.

In the context of the present disclosure the term "sexual dysfunction" denotes any condition that affects a sexual act of a man or a female, during any stage of a sexual act. The dysfunction can be life-long, acquired, situational, or generalized, occurring despite the situation.

Irrespective of the cause (psychological, physical or combination of same), a sexual dysfunction encompasses, depending on the gender, any condition selected from the group consisting of erectile dysfunction, premature ejaculation, ejaculatory incompetence, retarded ejaculation, sexual desire disorders (e.g. inhibited sexual desire, hypoactive sexual desire disorder, sexual aversion disorder), sexual arousal disorders (e.g. lack or reduced vaginal lubrication, reduced or lack of vaginal swelling, reduced muscle tone, lack or reduced erotic sensation), orgasm disorders, and sexual pain disorders.

When referring to "treatment" by the $A_3AR$ ligand it is to be understood to refer to any desired pharmacological and physiological effect that improves the sexual response (sexual function) in the treated subject. The improvement in sexual response may be any one or combination of increase in sexual desire, improvement in sexual arousal, stimulation or improvement in orgasm, and reduce or elimination of sexual pain. The improvement in sexual function may be subjective, i.e. based on the treated subject's feeling, or objective, based on physiological parameters, such as increased blood flow to the penis, increase in sperm motility, improved vaginal muscle tone and vaginal tissue health, enhanced vaginal lubrication.

In some exemplary embodiments, the $A_3AR$ ligand is effective to cause or improve erection. In some other exemplary embodiments, the $A_3AR$ ligand is effective to cause or improve sexual desire.

The $A_3AR$ ligand is used in an amount effective to treat the sexual dysfunction, namely, an amount which exhibits an effect of improving the sexual function or improving sexual feeling of the treated subject. The "effective amount" can be readily determined, in accordance with the invention, by administering to a plurality of tested subjects various amounts of the $A_3AR$ ligand and then plotting the response (for example combining several beneficial effects) as a function of the amount. At times, the amount to be used may depend on a variety of factors such as mode of administration, age, weight, body surface area, gender, health condition and genetic factors of the subject; other administered drugs; etc.

When referring to "$A_3$ adenosine receptor ligand" or "$A_3AR$ ligand" it is to be understood to mean any compound capable of directly (e.g. via the receptor binding site) or indirectly (e.g. via an allosteric binding site) modulating the activity of the $A_3$ adenosine receptor, this including full or partial activation of the $A_3$ adenosine receptor. The $A_3AR$ ligand is thus a molecule that exerts its prime effect through the enhancement of the activity of the $A_3AR$ irrespective of whether the activation is via the binding site or allosteric binding site. This means that at the doses it is being administered it essentially affects only the $A_3AR$.

Generally, the term "modulation" encompasses either enhancement (activation) or inhibition of the receptor activity, but in the context of the present disclosure, modulation primarily refers to enhancement.

In the context of the present disclosure, the "$A_3$ adenosine receptor ligand" encompasses $A_3AR$ agonists or $A_3AR$ allostaric enhancers.

When referring to "$A_3$ adenosine receptor agonist" or "$A_3AR$ agonist" it is to be understood to mean any ligand capable of specifically binding to the $A_3$ adenosine receptor, thereby fully or partially activating the $A_3$ adenosine receptor. The $A_3AR$ agonist is thus a molecule that exerts its prime effect through the binding and activation of the $A_3AR$. This means that at the doses it is being administered it essentially binds to and activates only the $A_3AR$.

In one embodiment, an $A_3AR$ agonist has a binding affinity ($K_i$) to the human $A_3AR$ in the range of less than 100 nM, typically less than 50 nM, preferably less than 20 nM, more preferably less than 10 nM and ideally less than 5 nM. Particularly preferred are $A_3AR$ agonists that have a $K_i$ to the human $A_3R$ of less than 2 nM and desirably less than 1 nM.

However, it should be understood that some $A_3AR$ agonists can also interact with and activate other receptors, however, with lower affinities (namely a higher Ki).

A molecule will be considered an $A_3AR$ agonist in the context of the present disclosure (namely a molecule that exerts its prime effect through the binding and activation $A_3AR$) if its affinity to the $A_3AR$ is at least 3 times (i.e. its Ki to the $A_3AR$ is at least 3 times lower), preferably 10 times, desirably 20 times and most preferably at least 50 times larger than the affinity to any other of the adenosine receptors (i.e. $A_1$, $A_{2a}$ and $A_{2b}$).

The affinity of an $A_3AR$ agonist to the human $A_3AR$ as well as its relative affinity to the other human adenosine receptors can be determined by a number of assays, such as a binding assay. Examples of binding assays include providing membranes containing a receptor and measuring the ability of the $A_3AR$ agonist to displace a bound radioactive agonist; utilizing cells that display the respective human adenosine receptor and measuring, in a functional assay, the ability of the $A_3AR$ agonist to activate or deactivate, as the case may be, downstream signaling events such as the effect on adenylate cyclase measured through increase or decrease of the cAMP level; etc. Clearly, if the administered level of an $A_3AR$ agonist is increased such that its blood level reaches a level approaching that of the Ki of the $A_1$, $A_{2a}$ and $A_{2b}$ adenosine receptors, activation of these receptors may occur following such administration, in addition to activation of the $A_3AR$. An $A_3AR$ agonist is thus preferably administered at a dose such that the blood level is such so that essentially only the $A_3AR$ will be activated.

In some embodiments, the $A_3AR$ agonist is a molecule that has a purine backbone. In some embodiment, the purine containing compound may be determined as an $A_3AR$ agonist based on acceptable structure-function activity assays.

The characteristic of some $A_3AR$ agonists and methods of their preparation are described in detail in, inter alia, U.S. Pat. No. 5,688,774; U.S. Pat. No. 5,773,423, U.S. Pat. No. 5,573,772, U.S. Pat. No. 5,443,836, U.S. Pat. No. 6,048,865, WO 95/02604, WO 99/20284, WO 99/06053, WO 97/27173 and WO 01/19360, all of which are incorporated herein by reference.

According to some embodiments of the present disclosure, the $A_3AR$ agonist is a purine derivative falling within the scope of the general formula (I):

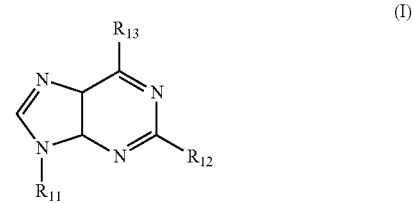

(I)

wherein, $R_{11}$ represents an alkyl, hydroxyalkyl, carboxyalkyl or cyanoalkyl or a group of the following general formula (II):

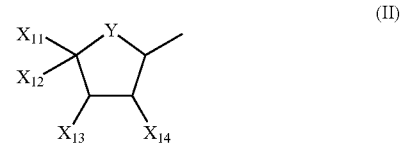

(II)

in which:

Y represents oxygen, sulfur or $CH_2$;

$X_{11}$ represents H, alkyl, $R^eR^fNC(=O)$— or $HOR^g$—, wherein $R^e$ and $R^f$ may be the same or different and are selected from the group consisting of hydrogen, alkyl, amino, haloalkyl, aminoalkyl, BOC-aminoalkyl, and cycloalkyl or are joined together to form a heterocyclic ring containing two to five carbon atoms; and $R^g$ is selected from the group consisting of alkyl, amino, haloalkyl, aminoalkyl, BOC-aminoalkyl, and cycloalkyl;

$X_{12}$ is H, hydroxyl, alkylamino, alkylamido or hydroxyalkyl;

$X_{13}$ and $X_{14}$ represent independently hydrogen, hydroxyl, amino, amido, azido, halo, alkyl, alkoxy, carboxy, nitrilo, nitro, trifluoro, aryl, alkaryl, thio, thioester, thioether, —OCOPh, —OC(=S)OPh or both $X_{13}$ and $X_{14}$ are oxygens connected to >C=S to form a 5-membered ring, or $X_{12}$ and $X_{13}$ form the ring of formula (III):

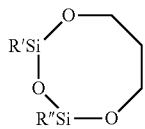

where R' and R" represent independently an alkyl group;

$R_{12}$ is selected from the group consisting of hydrogen, halo, alkylether, amino, hydrazido, alkylamino, alkoxy, thioalkoxy, pyridylthio, alkenyl; alkynyl, thio, and alkylthio; and $R_{13}$ is a group of the formula —$NR_{15}R_{16}$ wherein $R_{15}$ is a hydrogen atom or a group selected from alkyl, substituted alkyl or aryl-NH—C(Z)—, with Z being O, S, or $NR^a$ with $R^e$ having the above meanings; wherein when $R_{15}$ is hydrogen than $R_{16}$ is selected from the group consisting of R- and S-1-phenylethyl, benzyl, phenylethyl or anilide groups unsubstituted or substituted in one or more positions with a substituent selected from the group consisting of alkyl, amino, halo, haloalkyl, nitro, hydroxyl, acetoamido, alkoxy, and sulfonic acid or a salt thereof; benzodioxanemethyl, fururyl, L-propylalanyl-aminobenzyl, β-alanylamino-benzyl, T-BOC-β-alanylaminobenzyl, phenylamino, carbamoyl, phenoxy or cycloalkyl; or $R_{16}$ is a group of the following formula (IV):

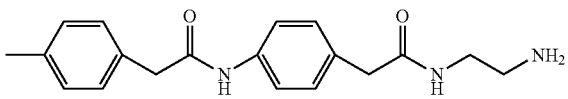

or when $R_{15}$ is an alkyl or aryl-NH—C(Z)—, then, $R_{16}$ is selected from the group consisting of heteroaryl-$NR^a$—C(Z)—, heteroaryl-C(Z)—, alkaryl-$NR^a$—C(Z)—, alkaryl-C(Z)—, aryl-NR—C(Z)— and aryl-C(Z)—; Z representing an oxygen, sulfor or amine.

Exemplary $A_3AR$ agonist (disclosed in U.S. Pat. No. 5,688,774 at column 4, lines 67-column 6, line 16; column 5, lines 40-45; column 6, lines 21-42; column 7, lines 1-11; column 7, lines 34-36; and column 7, lines 60-61):

$N^6$-(3-iodobenzyl)-9-methyladenine;
$N^6$-(3-iodobenzyl)-9-hydroxyethyladenine;
R—$N^6$-(3-iodobenzyl)-9-(2,3-dihydroxypropyl)adenine;
S—$N^6$-(3-iodobenzyl)-9-(2,3-dihydroxypropyl)adenine;
$N^6$-(3-iodobenzyladenin-9-yl)acetic acid;
$N^6$-(3-iodobenzyl)-9-(3-cyanopropyl)adenine;
2-chloro-$N^6$-(3-iodobenzyl)-9-methyladenine;
2-amino-$N^6$-(3-iodobenzyl)-9-methyladenine;
2-hydrazido-$N^6$-(3-iodobenzyl)-9-methyladenine;
$N^6$-(3-iodobenzyl)-2-methylamino-9-methyladenine;
2-dimethylamino-$N^6$-(3-iodobenzyl)-9-methyladenine;
$N^6$-(3-iodobenzyl)-9-methyl-2-propylaminoadenine;
2-hexylamino-$N^6$-(3-iodobenzyl)-9-methyladenine;
$N^6$-(3-iodobenzyl)-2-methoxy-9-methyladenine;
$N^6$-(3-iodobenzyl)-9-methyl-2-methylthioadenine;
$N^6$-(3-iodobenzyl)-9-methyl-2-(4-pyridylthio)adenine;
(1S,2R,3S,4R)-4-(6-amino-2-phenylethylamino-9H-purin-9-yl)cyclopentane-1,2,3-triol;
(1S,2R,3S,4R)-4-(6-amino-2-chloro-9H-purin-9-yl)cyclopentane-1,2,3-triol;
(±)-9-[2α,3α-dihydroxy-4β-(N-methylcarbamoyl)cyclopent-1β-yl)]-$N^6$-(3-iodobenzyl)-adenine;
2-chloro-9-(2'-amino-2',3'-dideoxy-β-D-5'-methyl-arabino-furonamido)-$N^6$-(3-iodobenzyl)adenine;
2-chloro-9-(2',3'-dideoxy-2'-fluoro-β-D-5'-methyl-arabino furonamido)-$N^6$-(3-iodobenzyl)adenine;
9-(2-acetyl-3-deoxy-β-D-5-methyl-ribofuronamido)-2-chloro-$N^6$-(3-iodobenzyl)adenine;
2-chloro-9-(3-deoxy-2-methanesulfonyl-β-D-5-methyl-ribofuronamido)-$N^6$-(3-iodobenzyl)adenine;
2-chloro-9-(3-deoxy-β-D-5-methyl-ribofuronamido)-$N^6$-(3-iodobenzyl)adenine;
2-chloro-9-(3,5-1,1,3,3-tetraisopropyldisiloxyl-β-D-5-ribofuranosyl)-$N^6$-(3-iodobenzyl)adenine;
2-chloro-9-(2',3'-O-thiocarbonyl-β-D-5-methyl-ribofuronamido)-$N^6$-(3-iodobenzyl)adenine;
9-(2-phenoxythiocarbonyl-3-deoxy-β-D-5-methyl-ribofuronamido)-2-chloro-$N^6$-(3-iodobenzyl)adenine;
1-(6-benzylamino-9H-purin-9-yl)-1-deoxy-N,4-dimethyl-β-D-ribofuranosiduronamide;
2-chloro-9-(2,3-dideoxy-β-D-5-methyl-ribofuronamido)-$N^6$-benzyladenine;
2-chloro-9-(2'-azido-2',3'-dideoxy-β-D-5'-methyl-arabino-furonamido)-$N^6$-benzyladenine;
2-chloro-9-(β-D-erythrofuranoside)-$N^6$-(3-iodobenzyl)adenine;
$N^6$-(benzodioxanemethyl)adenosine;
1-(6-furfurylamino-9H-purin-9-yl)-1-deoxy-N-methyl-β-D-ribofuranosiduronamide;
$N^6$-[3-(L-prolylamino)benzyl]adenosine-5'-N-methyluronamide;
$N^6$-[3-(β-alanylamino)benzyl]adenosine-5'-N-methyluronamide;
$N^6$-[3-(N-T-Boc-β-alanylamino)benzyl]adenosine-5'-N-methyluronamide
6-(N'-phenylhydrazinyl)purine-9-β-ribofuranoside-5'-N-methyluronamide;
6-(O-phenylhydroxylamino)purine-9-β-ribofuranoside-5'-N-methyluronamide;
9-(β-D-2',3'-dideoxyerythrofuranosyl)-$N^6$-[(3-β-alanylamino)benzyl]adenosine;
9-(β-D-erythrofuranoside)-2-methylamino-$N^6$-(3-iodobenzyl)adenine;
2-chloro-N-(3-iodobenzyl)-9-(2-tetrahydrofuryl)-9H-purin-6-amine;
2-chloro-(2'-deoxy-6'-thio-L-arabinosyl)adenine; and
2-chloro-(6'-thio-L-arabinosyl)adenine.

Other exemplary $A_3AR$ agonists, disclosed in U.S. Pat. No. 5,773,423, are compounds of the formula (V):

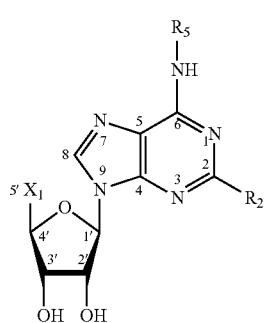

(V)

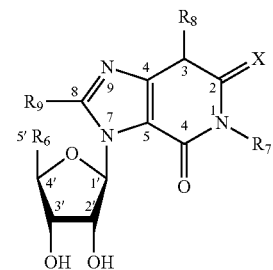

(VI)

wherein $X_1$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_2$ is selected from the group consisting of hydrogen, halo, $C_1$-$C_{10}$ alkyoxy, amino, $C_2$-$C_{10}$ alkenyl, and $C_2$-$C_{10}$ alkynyl; and $R_5$ is selected from the group consisting of R- and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo.

More specific compounds include those of the above formula wherein $R^a$ and $R^b$ may be the same or different and are selected from the group consisting of hydrogen and $C_1$-$C_{10}$ alkyl, particularly when $R_2$ is hydrogen or halo, especially hydrogen.

Additional specific compounds are those compounds wherein $R^a$ is hydrogen and $R_2$ is hydrogen, particularly when $R_5$ is unsubstituted benzyl.

More specific compounds are such compounds wherein $R^b$ is a $C_1$-$C_{10}$ alkyl or $C_3$-$C_{10}$ cycloalkyl, particularly a $C_1$-$C_{10}$ alkyl, and more particularly methyl.

Especially specific are those compounds where $R^a$ is hydrogen, $R^b$ is $C_1$-$C_{10}$ alkyl or $C_3$-$C_{10}$ cycloalkyl, and $R_5$ is R- or S-1-phenylethyl or a benzyl substituted in one or more positions with a substituent selected from the group consisting of halo, amino, acetamido, $C_1$-$C_{10}$ haloalkyl, and sulfo, where the sulfo derivative is a salt, such as a triethylammonium salt.

An example of an especially preferred compound disclosed in U.S. Pat. No. 5,773,423 is $N^6$-(3-iodobenzyl)-2-methylamino-9-[5-(methylamido)-β-D-ribofuranosyl]-adenine, also known as $N^6$-(3-iodobenzyl)-adenosine-5'-N-methyluronamide or known as 1-Deoxy-1-[6-[[(3-iodophenyl)methyl]amino]-9H-purine-9-yl]-N-methyl-D-ribofuranuronamide, or by the abbreviation IB-MECA.

In addition, those compounds in which $R_2$ is a $C_2$-$C_{10}$ alkenylene of the formula $R^d$—C=C— where $R^d$ is a $C_1$-$C_8$ alkyl are also particularly noted in U.S. Pat. No. 5,773,423.

Also specific are those compounds wherein $R_2$ is other than hydrogen, particularly those wherein $R_2$ is halo, $C_1$-$C_{10}$ alkylamino, or $C_1$-$C_{10}$ alkylthio, and, more preferably, when additionally $R^a$ is hydrogen, $R^b$ is a $C_1$-$C_{10}$ alkyl, and/or $R_5$ is a substituted benzyl.

Further exemplary $A_3AR$ agonists disclosed in U.S. Pat. No. 5,773,423 are modified xanthine-7-ribosides having the formula (VI):

wherein

X is O;

$R_6$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;

$R_7$ and $R_8$ may be the same or different and are selected from the group consisting of $C_1$-$C_{10}$ alkyl, R- and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo; and $R_9$ is selected from the group consisting of halo, benzyl, phenyl, and $C_3$-$C_{10}$ cycloalkyl.

WO 99/06053 discloses in examples 19-33 compounds selected from:

$N^6$-(4-biphenyl-carbonylamino)-adenosine-5'-N-ethyluronamide;

$N^6$-(2,4-dichlorobenzyl-carbonylamino)-adenosine-5'-N-ethyluronamide;

$N^6$-(4-methoxyphenyl-carbonylamino)-adenosine-5'-N-ethyluronamide;

$N^6$-(4-chlorophenyl-carbonylamino)-adenosine-5'-N-ethyluronamide;

$N^6$-(phenyl-carbonylamino)-adenosine-5'-N-ethyluronamide;

$N^6$-(benzylcarbamoylamino)-adenosine-5'-N-ethyluronamide;

$N^6$-(4-sulfonamido-phenylcarbamoyl)-adenosine-5'-N-ethyluronamide;

$N^6$-(4-acetyl-phenylcarbamoyl)-adenosine-5'-N-ethyluronamide;

$N^6$-((R)-α-phenylethylcarbamoyl)-adenosine-5'-N-ethyluronamide;

$N^6$-((S)-α-phenylethylcarbamoyl)-adenosine-5'-N-ethyluronamide;

$N^6$-(5-methyl-isoxazol-3-yl-carbamoyl)-adenosine-5'-N-ethyluronamide;

$N^6$-(1,3,4-thiadiazol-2-yl-carbamoyl)-adenosine-5'-N-ethyluronamide;

$N^6$-(4-n-propoxy-phenylcarbamoyl)-adenosine-5'-N-ethyluronamide;

$N^6$-bis-(4-nitrophenylcarbamoyl)-adenosine-5'-N-ethyluronamide; and $N^6$-bis-(5-chloro-pyridin-2-yl-carbamoyl)-adenosine-5'-N-ethyluronamide.

More specifically disclosed compounds include:

2-chloro-$N^6$-(3-iodobenzyl)-9-[5-(methylamido)-β-D-ribofuranosyl]adenine also known as 2-chloro-$N^6$-(3-iodobenzyl)-adenosine-5'-N-methyluronamide or by the abbreviation Cl-IB-MECA;

N⁶-(3-iodobenzyl)-2-methylamino-9-[5-(methylamido)-β-D-ribofuranosyl]-adenine, also known as N⁶-(3-iodobenzyl)-adenosine-5'-N-methyluronamide or known as 1-Deoxy-1-[6-[[(3-iodophenyl)methyl]amino]-9H-purine-9-yl]-N-methyl-D-ribofuranuronamide or by the abbreviation IB-MECA;

N⁶-2-(4-aminophenyl)ethyladenosine (APNEA);

N⁶-(4-amino-3-iodobenzyl)adenosine-5'-(N-methyluronamide) (AB-MECA).

In one particular embodiment, IB-MECA is used in the treatment of sexual dysfunction, accordance with the present disclosure.

When referring to "$A_3AR$ allosteric enhancement" it is to be understood as referring to the positive regulation, activation or incense of the receptor activity by binding of the allosteric effector molecule at the receptor's allosteric site which may be different from the binding site of the endogenous ligand or agonist thereof.

In some embodiments, the "$A_3AR$ allosteric enhancement" is by an imidazoquinoline derivative, namely, the allosteric enhancer is an imidazoquinoline derivative.

In this contexts, the term "enhancement" is to be understood as denoting an effect of the effector compound on the receptor exhibited by an increase of at least 15% in the efficacy of the $A_3$ adenosine receptor by binding of the effector compound to the allosteric site of the receptor and/or by a decrease in dissociation rate of adenosine or an $A_3AR$ agonist to the orthosteric binding site.

In some embodiments the $A_3AR$ enhancer, or imidazoquinoline derivative has the following general formula (VII):

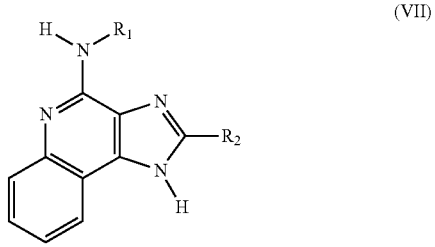

wherein:

$R_1$ represents an aryl or alkaryl being optionally substituted at the aromatic ring once or more with a substituent selected $C_1$-$C_{10}$ alkyl, halo, $C_1$-$C_{10}$ alkanol, hydroxyl, $C_1$-$C_{10}$ acyl, $C_1$-$C_{10}$ alkoxyl; $C_1$-$C_{10}$-alkoxycarbony, $C_1$-$C_{10}$ alkoxylalkyl; $C_1$-$C_{10}$ thioalkoxy; $C_1$-$C_{10}$ alkylether, amino, hydrazido, $C_1$-$C_{10}$ alkylamino, pyridylthio, $C_2$-$C_{10}$ alkenyl; $C_2$-$C_{10}$ alkynyl, thio, and $C_1$-$C_{10}$ alkylthio, acetoamido, sulfonic acid; or said substituents can form together a cycloalkyl or cycloalkenyl fused to said aryl, the cycloalkyl or cycloalkenyl optionally comprising one or more heteroatoms; provided that said aryl is not an unsubstituted phenyl group;

$R_2$ represents hydrogen or a substituent selected from $C_1$-$C_{10}$ alkyl, $C_2$-$C_{10}$ alkenyl; $C_2$-$C_{10}$ alkynyl, $C_4$-$C_{10}$ cycloalkyl, $C_4$-$C_{10}$ cycloalkenyl or a five to seven membered heterocyclic aromatic ring, $C_5$-$C_{15}$ fused cycloalkyl, bicyclic aromatic or heteroaromatic rings; or $C_1$-$C_{10}$ alkylether, amino, hydrazido, $C_1$-$C_{10}$ alkylamino, $C_1$-$C_{10}$ alkoxy, $C_1$-$C_{10}$-alkoxycarbony, $C_1$-$C_{10}$ alkanol, $C_1$-$C_{10}$ acyl, $C_1$-$C_{10}$ thioalkoxy, pyridylthio, thio, and $C_1$-$C_{10}$ alkylthio, acetoamido, sulfonic acid; and pharmaceutically acceptable salts thereof.

According to some embodiments, the $R_1$ substituent in the $A_3RM$ has the following general formula (VIII):

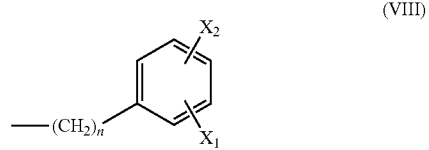

wherein n is 0 or an integer selected from 1-5; preferably, n is 0, 1 or 2; and $X_1$ and $X_2$ which may be the same or different, are selected from hydrogen halogen, alkyl, alkanol or alkoxy, indanyl, pyrroline provided that when said n is 0, $X_1$ and $X_2$ are not hydrogen.

In yet some further embodiments, $R_1$ in $A_3RM$ is a substituent having the above formula (VIII), wherein $X_1$ or $X_2$, which may be the same or different, are selected from hydrogen, chloro, methoxy, methanol or a substituent having the formulae (VIIIa) or (VIIIb):

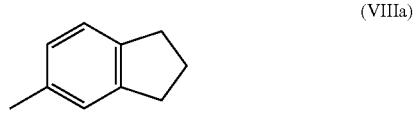

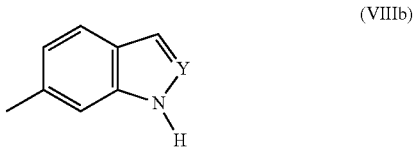

wherein Y is selected from N or CH.

In some yet further embodiments $R_2$ in $A_3RM$ is selected from H, $C_{1-10}$ alkyl, $C_{4-10}$ cycloalkyl, the alkyl chain may be a straight or branched or form a four to seven membered cycloalkyl ring.

In yet some further embodiments, $R_2$ in $A_3RM$ is selected from a five to seven membered heterocyclic aromatic ring.

In some embodiments, $R_2$ substituents in $A_3RM$ are selected from H, n-pentyl, or a five membered heterocyclic aromatic ring having the following formula (IX):

wherein Z is selected from O, S or NH, preferably O.

In accordance with some embodiments $R_2$ in $A_3RM$ comprises one or more fused rings, particularly so as to form bicyclic substituents.

Non-limiting examples of bicyclic compounds which may be used to form the substituents in the context of the invention comprise bicyclo[2.2.1]heptane, bicyclo[4.1.0]heptane, bicyclo[4.1.0]heptan-3-carboxylic acid, bicyclo[3.1.0]hexan-3-carboxylic acid, bicyclo[4.1.0]heptan-2-carboxylic acid, bicyclo[3.1.0]hexan-2-carboxylic acid, and bicyclo[2.2.1]heptan-2-carboxylic acid.

In accordance with yet some other embodiments, $R_2$ in $A_3RM$ may be selected from 2-cyclohexene and 3-cyclohexene.

Specific imidazoquinoline derivatives which may be used as allosteric effectors of the $A_3AR$ are listed below:

N-(4-Methyl-phenyl)-2-cyclopentyl-1H-imidazo[4,5-c]quinolin-4-amine

N-(4-Methoxy-phenyl)-2-cyclopentyl-1H-imidazo[4,5-c]quinolin-4-amine

N-(3,4-Dichloro-phenyl)-2-cyclopentyl-1H-imidazo[4,5-c]quinolin-4-amine

N-(4-Chloro-phenyl)-2-cyclopentyl-1H-imidazo[4,5-c]quinolin-4-amine

N-(3-Methanol-phenyl)-2-cyclopentyl-1H-imidazo[4,5-c]quinolin-4-amine

N-([3,4-c]Indan)-2-cyclopentyl-1H-imidazo[4,5-c]quinolin-4-amine

N-(1H-indazol-6-yl)-2-cyclopentyl-1H-imidazo[4,5-c]quinolin-4-amine

N-(4-Methoxy-benzyl)-2-cyclopentyl-1H-imidazo[4,5-c]quinolin-4-amine

N-(1H-Indol-6-yl)-2-cyclopentyl-1H-imidazo[4,5-c]quinolin-4-amine

N-(Benzyl)-2-cyclopentyl-1H-imidazo[4,5-c]quinolin-4-amine

N-(Phenylethyl)-2-cyclopentyl-1H-imidazo[4,5-c]quinolin-4-amine

N-(3,4-Dichloro-phenyl)-2-cycloheptyl-1H-imidazo[4,5-c]quinolin-4-amine

N-(3,4-Dichloro-phenyl)-2-furyl-1H-imidazo[4,5-c]quinolin-4-amine

N-(3,4-Dichloro-phenyl)-2-cyclobutyl-1H-imidazo[4,5-c]quinolin-4-amine

N-(3,4-Dichloro-phenyl)-2-cyclohexyl-1H-imidazo[4,5-c]quinolin-4-amine

N-(3,4-Dichloro-phenyl)-2-1H-imidazo[4,5-c]quinolin-4-amine

N-(3,4-Dichloro-phenyl)-2-pentyl-1H-imidazo[4,5-c]quinolin-4-amine.

The above imidazoquinoline derivatives are regarded as allosteric effectors (modulating the activity) as they where shown to have, on the one hand, reduced affinity, if any, to the orthosteric binding sites of the $A_1$ and $A_{2A}$, $A_{2B}$ adenosine receptors and reduced affinity to the orthosteric binding site of the $A_3$ adenosine receptor, and on the other hand, high affinity to the allosteric site of the $A_3$ adenosine receptor [International Patent Application No. WO07/089507, incorporated herein by reference].

In some embodiments, the imidazoquinoline derivatives provided above are of a kind that increases the activity of the $A_3AR$. Thus, in accordance with some preferred embodiments modulation concerns enhancement of $A_3AR$ activity. In this context, the imidazoquinoline derivatives are considered as $A_3AR$ activators or enhancers. In this contexts, the term "enhancement" is to be understood as denoting an effect of the imidazoquinoline derivative on the receptor exhibited by an increase of at least 15% in the efficacy of the $A_3$ adenosine receptor by binding of the imidazoquinoline to the allosteric site of the receptor and/or by a decrease in dissociation rate of adenosine or an $A_3AR$ agonist to the orthosteric binding site.

A specifically preferred imidazoquinoline derivative in accordance with the present disclosure is N-(3,4-Dichlorophenyl)-2-cyclohexyl-1H-imidazo[4,5-c]quinolin-4-amine (also referred to at times by the abbreviation LUF6000 or CF602), being an allosteric enhancer.

In the context of the general formulae disclosed herein, the following meaning for the various terms is to be considered:

The term "alkyl" is used herein to refer to a linear or branched hydrocarbon chain having from 1 to 10 carbon atoms and more preferably 1 to 6 carbon atoms including, but not limited to, methyl, ethyl, n-propyl, isopropyl, n-butyl, t-butyl, n-heptyl, octyl and the like.

Similarly, the terms "alkenyl" and "alkynyl" denote a linear or branched hydrocarbon chain having, respectively, from 2 to 10, or from 3 to 10 carbon atoms and more preferably 2 to 6 or 3 to 6 carbon atoms, the alkenyl or alkynyl having at least one unsaturated bond.

The alkyl, alkenyl or alkynyl substituents may be substituted with a heteroatom containing group. Thus, it should be understood that while not explicitly stated, any of the alkyl modifications defined hereinabove and below, such as alkylthio, alkoxy, akanol, alkylamine etc, also include the corresponding alkenyl or alkynyl modifications, such as, akenylthio, akenyloxy, alkenol, alkenylamine, or respectively, akynylthio, alkynyloxy, alkynol, alkynylamine.

The term "aryl" denotes an unsaturated aromatic carbocyclic group of from 5 to 14 carbon atoms having a single ring (e.g., phenyl) or multiple condensed rings (e.g., naphthyl or anthryl). Preferred aryls include phenyl, indanyl, benzimidazole.

The term "alkaryl" refers to -alkylene-aryl groups preferably having from 1 to 10 carbon atoms in the alkylene moiety and from 6 to 14 carbon atoms in the aryl moiety. Such alkaryl groups are exemplified by benzyl, phenethyl and the like.

The term "Substituted aryl" refers to an aromatic moiety which is substituted with from 1 to 3 substituents as defined above. A variety of substituents are possible, as appreciated by those versed in the art. Nonetheless, some preferred substituents include, without being limited thereto, halogen, (substituted) amino, nitro, cyano, alkyl, alkoxy, acyloxy or alkanol, sulphonyl, sulphynyl.

The term "Halo" or "halogen" refers to fluoro, chloro, bromo and iodo, preferably to chloro.

The term "acyl" refers to the groups H—C(O)— as well as alkyl-C(O)—.

The term "alkanol" refers to the group —COH as well as alk-OH, "alk" denoting an alkylene, alkenylene or alkynylene chain.

The term "alkoxy" is used herein to mean —O-alkyl, including, but not limited to, methoxy, ethoxy, propoxy, isopropoxy, n-butoxy and the like.

The term "alkylthio" is used herein to mean —S-alkyl, including, but not limited to, methylthio, ethylthio, n-propylthio, isopropylthio, n-butylthio and the like.

The term "alkoxyalkyl" is used herein to mean -alkyl-O-alkyl, including, but not limited to, methoxymethyl, ethoxymethyl, n-propoxymethyl, isopropoxymethyl, n-butoxymethyl, isobutoxymethyl, t-butoxymethyl and the like.

The term "cycloalkyl" is used herein to mean cyclic hydrocarbon radicals including, but not limited to, cyclopropyl, cyclobutyl, cyclopentyl, cyclohexyl, cycloheptyl and the like.

The term "alkoxycarbonyl" is used herein to mean —C(O)O-alkyl, including, but not limited to, methoxycarbonyl, ethoxycarbonyl, propoxycarbonyl and the like.

The term "fused cycloalkyl" is used herein to mean any compound or substituent comprising at least two aliphatic rings which are connected at a single atom (to form a spirocyclic moiety), at two mutually bonded atoms or across a sequence of atoms (bridgehead). The fused rings may include any bicyclic, tricyclic as well as polycyclic moieties. Bicyclic substituents are preferred in accordance with some embodiments of the present disclosure.

The present disclosure also makes use of physiologically acceptable salts of an $A_3AR$ ligand, such as the above disclosed compounds. An "physiologically acceptable salts" refers to any non-toxic alkali metal, alkaline earth metal, and ammonium salt commonly used in the pharmaceutical industry, including the sodium, potassium, lithium, calcium, magnesium, barium ammonium and protamine zinc salts, which are prepared by methods known in the art. The term also includes non-toxic acid addition salts, which are generally prepared by reacting the ligand with a suitable organic or inorganic acid. The acid addition salts are those which retain the biological effectiveness and qualitative properties of the free bases and which are not toxic or otherwise undesirable. Examples include, inter alia, acids derived from mineral acids, hydrochloric, hydrobromic, sulfuric, nitric, phosphoric, metaphosphoric and the like. Organic acids include, inter alia, tartaric, acetic, propionic, citric, malic, malonic, lactic, fumaric, benzoic, cinnamic, mandelic, glycolic, gluconic, pyruvic, succinic salicylic and arylsulphonic, e.g. p-toluenesulphonic, acids.

In the following, unless otherwise indicated, dosages are indicated either in weight per dosage form or in weight/Kg, meaning weight of administered $A_3AR$ ligand per kilogram of body weight of the treated subject in each administration (for example, mg/Kg and microgram/Kg denote, respectively, milligrams of administered ligand and micrograms of administered ligand per kilogram of body weight of the treated subject).

Thus, in some embodiment which encompass the $A_3AR$ agonist as the ligand, an effective amount is less than about 1 mg/kg body weight, particularly less than about 500 μg/kg or even less than about 200 μg/kg body weight or at times less than about 100 μg/kg body weight or even less than about less than 50 μg/kg body weight. Similar amounts, at times, the same amounts, are to be used, in accordance with some embodiments, where the $A_3AR$ ligand is an allosteric enhancer of the receptor.

The effective amount may also be defined by a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

Accordingly, when referring to the agonist IB-MECA, the effective amount is preferably less than 5 mg per dose, for once daily administration (namely a dose less than about 70 μg/kg body weight, assuming an average individual weight of about 70 kg), and less than about 4 mg each dose (i.e. less than about 57 μg/kg body weight), for twice daily administration. The dose of IB-MECA is more preferably less than about 2 mg each dose and typically between about 0.1-1 mg each dose, for either once or twice daily administration (the corresponding dosages in weight per body weight being about 29 μg/kg and about 1.5-15 μg/kg body weight, respectively).

In accordance with some other embodiments that encompass the allosteric enhancers as the ligand, the effective amount in a unit dosage form may vary from about 0.5 mg to 500 mg.

The administration of the $A_3AR$ ligand to an individual may be together with a pharmaceutically acceptable carrier to form a dosage form suitable for a specific mode of administration. By the term "pharmaceutically acceptable carrier" it is meant any one of inert, non-toxic materials, which do not react with the $A_3AR$ ligand and which can be added to formulations as diluents or carriers or to give form or consistency to the formulation.

The dosage form is thus the physical form of $A_3AR$ ligand used in the composition to be administered to the subject in need thereof. It is thus in the context of the present disclosure that also provided are pharmaceutical compositions comprising a physiologically acceptable carrier, and the $A_3AR$ ligand as the active agent.

The composition may be formulated in various administration forms, including oral administration and topical (local) administration.

In the case where administration is oral, the carrier is one that is acceptable for preparation of a dosage form suitable for oral administration. In the case where the administration is topical, the carrier is one that is acceptable for formulating a dosage form suitable for topical administration.

An oral formulation may be in the form of a pill, capsule, in the form of a syrup, emulsion, an aromatic powder, and other various forms. The carrier is selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc. The carriers may be any of those conventionally used and is limited only by chemical-physical considerations, such as solubility and lack of reactivity with the $A_3AR$ ligand, and by the route of administration. The carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way.

Typical examples of carriers suitable for oral administration comprise (a) suspensions or emulsions in an appropriate liquid such as Cremophor RH40, or methylcellulose (e.g. Methocel A4M Premium); (b) capsules (e.g. the ordinary hard- or soft-shelled gelatin type containing, for example, surfactants, lubricants, and inert fillers), tablets, lozenges (wherein the active substance is in a flavor, such as sucrose and acacia or tragacanth or the active substance is in an inert base, such as gelatin and glycerin), and troches, each containing a predetermined amount of the tragacanth as solids or granules; (c) powders; (d) solution, typically when combined with a solubilizing enhancing agent; (e) liposome formulation; and others.

One non limiting example for an oral administration form of the $A_3AR$ ligand, IB-MECA includes the following ingredients and amounts formulated in the form of tablets:

TABLE 1

IB-MECA Tablets

|  | Ingredient | Amount (mg) |
|---|---|---|
| Intragranular | IB-MECA | 1.000 |
|  | Pregelatinized Starch | 10.00 |
|  | Croscarmellose Sodium | 2.000 |
|  | Lactose Monohydrate 310 | 64.25 |
|  | Microcrystalline Cellulose | 20.00 |

TABLE 1-continued

IB-MECA Tablets

| | Ingredient | Amount (mg) |
|---|---|---|
| Extragranular | Croscarmellose Sodium | 2.000 |
| | Magnesium Stearate | 0.7500 |
| | Total | 100.00 |
| Coating | Opadry White | 3.000 |
| | Total | 103.0 |

In case the composition if formulated for topical (local) administration, the composition may be in the form suitable for application onto the penis, such as, without being limited thereto, a cream, a gel or a patch; or in the form suitable for application over a portion of the wall of the female genital tract, preferably to a portion of the inner wall of the vagina, such as, without being limited thereto, in the form of a vaginal suppository, a tampon impregnated with the composition comprising the ligand, a cream or gel to be applied using a applicator such as those used self administer contraceptive foams.

For the purpose of topical administration, the carrier is preferably selected from amongst those which enhance tissue penetration of the $A_3AR$ ligand and may include, without being limited to, glycerine, lubricants, olive oil, nitroglycerine, glyceryl monocaprylate, propylene glycol didecanoate, propylene glycol dicaprylate, glyceryl tricaprylate, sorbitan monocaprylate, and mixtures thereof. Pharmaceutical creams, viscous liquid or semi-solid emulsion containing oil phase and water-based phase can be prepared as described by Philip P. Gerbino, in "*Remington: the science and practice of pharmacy*" 21st edition Publisher: Lippincott Williams & Wilkins, (2005).

Irrespective of the mode of administration, application of the ligand, i.e. treatment may be acute treatment, e.g. prior to intercourse, or long term treatment.

As used herein, the forms "a", "an" and "the" include singular as well as plural references unless the context clearly dictates otherwise. For example, the term "an $A_3AR$ ligand" includes one or more compounds which are capable of specifically affecting, directly or indirectly, fully or partially, the activity of the $A_3AR$.

Further, as used herein, the term "comprising" is intended to mean that the composition include the recited active agent, i.e. $A_3AR$ ligand, but not excluding other elements, such as physiologically acceptable carriers and excipients as well as other active agents. The term "consisting essentially of" is used to define compositions which include the recited elements but exclude other elements that may have an essential significance on treatment of uveitis. "Consisting of" shall thus mean excluding more than trace elements of other elements. Embodiments defined by each of these transition terms are within the scope of this invention.

Further, all numerical values, e.g. when referring the amounts or ranges of the elements constituting the composition comprising the $A_3AR$ ligand as an active ingredient, are approximations which are varied (+) or (−) by up to 20%, at times by up to 10% of from the stated values. It is to be understood, even if not always explicitly stated that all numerical designations are preceded by the term "about".

The invention will now be exemplified in the following description of experiments that were carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow

NON-LIMITING EXAMPLES

Example 1

Clinical Study (I) with IB-MECA (CF101), an $A_3AR$ Agonist

The clinical study (the "Study") was a Phase 3, Randomized, Double-Masked, Placebo-Controlled, Dose-Finding, Parallel-Group Study of the Safety and Efficacy of Daily CF101 Administered Orally in Patients with Moderate-to-Severe Dry Eye Disease, keratoconjunctivitis sicca (KCS). CF101 is an experimental pharmaceutical composition where the active ingredient is IB-MECA. The study had two primary objectives: (i) determine the efficacy of oral administered CF101, as compared to placebo, when administered at doses of either 0.1 mg or 1.0 mg (namely 0.1 and 1 mg of IB-MECA per each administration, respectively) twice daily for 24 weeks in patients with KCS, and (ii) determine the safety of this drug in the patients.

Patients were randomized to receive pills of either CF101 0.1 mg, CF101 1.0 mg, or matching placebo, given orally twice daily (BID) for 24 weeks. A Screening Period of up to 4 weeks that includes a 2-week run-in period that preceded the 24-week treatment period, followed by a 2-week follow-up period.

The patients that were enrolled in the study had to meet a number of inclusion criteria (namely criteria that had to be matched for a human subject to participate in the study), including (i) being 18 years of age and over, (ii) being diagnosed with moderate-to-severe Aqueous-Deficient Dry Eye (including Sjögren's Syndrome dry eye), as defined by acceptable clinical criteria, and (iii) a variety of other criteria. Patients that met certain exclusion criteria that related to certain ophthalmic conditions and use of other medications.

Clinical outcome in improving KCS symptoms was determined through a variety of relevant ophthalmic parameters. In addition, adverse events were recorded for each patient throughout the study and all effects reported by patients were reported.

By the time of filing this patent application the study was still ongoing. Reported, below, however, are two reported patient-related events, each from a different patient, that demonstrate are clinical effects as provided for by the present disclosure. It should be noted that at this time of reporting of these events the study was still masked, namely it is not known whether the patients received CF101 or placebo and if CF101 than the dose of the drug. However, the reported effects suggest that the patients received CF101 at a dose of either 0.1 mg or 1 mg (twice daily over the study period).

The first patient (a patient designated by the code 104507) was a 71 years old patient. The patient reported an increase of sexual potency related to CF101 intake.

The second patient was a 36 years old patient. He reported an unprovoked erection after intake of CF101. Patient noted that he strongly believes that the event is directly caused by CF101. The patient described that around 30 minutes after intake he had unprovoked erection every day after each CF101 intake for about 10 days.

Example 2

Clinical Study (II) with IB-MECA (CF101), an A3AR Agonist

Phase 2 study in patients with active rheumatoid arthritis (RA) (randomized, double-blind, placebo-controlled), treated in parallel with CF101 administrated orally when added to weekly Methotrexate (MTX). The patients were given CF101 either 0.1 mg or 1 mg tablets or placebo tablets, taken orally every 12 h for 12 weeks. Washout of other disease-modifying antirheumatic drugs (DMARDs), including biological agents was occurring prior to dosing.

In the study, some of the patients experienced erection or increase in sexual desire during treatment in CF101.

In a further Phase 2 study, randomized, double-blind, dose-ranging, placebo-controlled study was conducted to determine safety and activity of CF101 administered orally in patients with moderated to severe Plaque Psoriasis (PS). CF101 was administered at 1 mg. 2 mg and 4 mg twice daily for 12 weeks.

Patient enrolled for this study did not received systemic retinoids, corticosteroids or immunosuppressants within 6 weeks prior to initiation of the study.

In the study, some of the patients experienced erection or increase in sexual desire during treatment in CF101.

The above studies show that irrespective of the original reason for administration of CF101 (i.e. the original condition to be treated with CF101), an non-neglectable number of patients experienced erection or increase in sexual desire.

Example 3

Animal Model Treatment with Allosteric Enhancer CF602

Male C57BL/6j mice, 8 weeks of age, were injected intravenously (tail vein) with concanavalin A (Con.A) (20 mg/kg). twenty four hours after Con.A injection, levels of alanine aminotransferase (ALT) and aspirate aminotransferase (AST) were measured in the serum.

The allosteric compound, Luf6000 (also known as N-(3, 4-dichloro-phenyl)-2-cyclohexyl-1H-imidazo[4,5-c]quinolin-4-amine), was orally administered at a dose of 100 µg/kg 8 h after Con.A administration and 2 h before termination.

Results

Before experiment termination, erection was noticed in the Luf6000 treated group with no signs of erection in the control-untreated group.

The invention claimed is:

1. A method of treating a sexual dysfunction comprising administering to a subject having erectile dysfunction an effective amount of an $A_3$ adenosine receptor ($A_3AR$) ligand selected from the group consisting of (i) an $A_3AR$ agonist of formula (V)

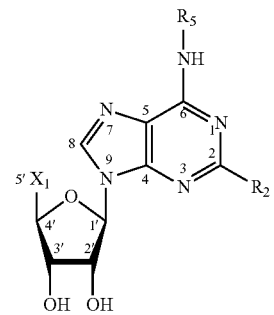

wherein
$X_1$ is $R^aR^bNC(=O)$, wherein $R^a$ and $R^b$ may be the same or different and are selected from the group consisting of hydrogen, $C_1$-$C_{10}$ alkyl, amino, $C_1$-$C_{10}$ haloalkyl, $C_1$-$C_{10}$ aminoalkyl, and $C_3$-$C_{10}$ cycloalkyl;
$R_2$ is selected from the group consisting of hydrogen, halo, $C_1$-$C_{10}$ alkyoxy, amino, $C_2$-$C_{10}$ alkenyl, and $C_2$-$C_{10}$ alkynyl; and
$R_5$ is selected from the group consisting of R- and S-1-phenylethyl, an unsubstituted benzyl group, and a benzyl group substituted in one or more positions with a substituent selected from the group consisting of $C_1$-$C_{10}$ alkyl, amino, halo, $C_1$-$C_{10}$ haloalkyl, nitro, hydroxy, acetamido, $C_1$-$C_{10}$ alkoxy, and sulfo, (ii) an $A_3AR$ allosteric enhancer of formula (VII)

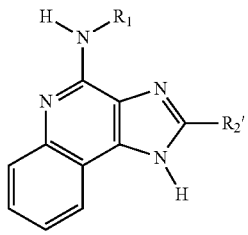

wherein:
$R_1$ represents an aryl or alkaryl being optionally substituted at the aromatic ring with one or more substituents selected from the group consisting of $C_1$-$C_{10}$ alkyl, halo, $C_1$-$C_{10}$ alkanol, hydroxyl, $C_1$-$C_{10}$ acyl, $C_1$-$C_{10}$ alkoxyl, $C_1$-$C_{10}$-alkoxycarbony, $C_1$-$C_{10}$ alkoxylalkyl, $C_1$-$C_{10}$ thioalkoxy, $C_1$-$C_{10}$ alkylether, amino, hydrazido, $C_1$-$C_{10}$ alkylamino, pyridylthio, $C_2$-$C_{10}$ alkenyl, $C_2$-$C_{10}$ alkynyl, thio, $C_1$-$C_{10}$ alkylthio, acetoamido, and sulfonic acid; or said substituents can form together a cycloalkyl or cycloalkenyl fused to said aryl, the cycloalkyl or cycloalkenyl optionally comprising one or more heteroatoms; provided that said aryl is not an unsubstituted phenyl group;
$R_2'$ represents hydrogen or a substituent selected from the group consisting of $C_1$-$C_{10}$ alkyl, $C_2$-$C_{10}$ alkenyl, $C_2$-$C_{10}$ alkynyl, $C_4$-$C_{10}$ cycloalkyl, $C_4$-$C_{10}$ cycloalkenyl, a five to seven membered heterocyclic aromatic ring, $C_5$-$C_{15}$ fused cycloalkyl, bicyclic aromatic or heteroaromatic rings, $C_1$-$C_{10}$ alkylether, amino, hydrazido, $C_1$-$C_{10}$ alkylamino, $C_1$-$C_{10}$ alkoxy, $C_1$-$C_{10}$-alkoxycarbony, $C_1$-$C_{10}$ alkanol, $C_1$-$C_{10}$ acyl, $C_1$-$C_{10}$ thioalkoxy, pyridylthio, thio, $C_1$-$C_{10}$ alkylthio, acetoamido, and sulfonic acid;
and pharmaceutically acceptable salts thereof.

2. The method of claim 1, comprising oral administration of the $A_3AR$ ligand.

3. The method of claim 2, comprising oral administration once or twice a day.

4. The method of claim 3, comprising oral administration twice a day.

5. The method of claim 1, wherein said $A_3AR$ ligand is an $A_3AR$ agonist and said method comprises oral administration twice a day of an amount of said $A_3AR$ agonist of between 0.05 mg to 2 mg per dosage form.

6. The method of claim 1, wherein said $A_3AR$ ligand is an $A_3AR$ agonist and said method comprises oral administration twice a day of an amount of said $A_3AR$ agonist of between 0.1 mg to 1.0 mg per dosage form.

7. The method of claim 1, wherein said $A_3AR$ ligand is an $A_3AR$ allosteric enhancer and said method comprises oral administration twice a day of an amount of said $A_3AR$ allosteric enhancer of between 0.1 mg to 500 mg per dosage form.

8. The method of claim 1, comprising topical administration of said $A_3AR$ agonist over the subject's genital organ.

9. The method of claim 1, wherein the $A_3AR$ ligand is an $A_3AR$ agonist selected from the group consisting of $N^6$-2-(4-aminophenyl)ethyladenosine (APNEA), $N^6$-(4-amino-3-iodobenzyl) adenosine-5'-(N-methyluronamide) (AB-MECA), $N^6$-(3-iodobenzyl)-adenosine-5'-N-methyluronamide (IB-MECA) and 2-chloro-$N^6$-(3-iodobenzyl)-adenosine-5'-N-methyluronamide (Cl-IB-MECA).

10. The method of claim 9, wherein the $A_3AR$ agonist is IB-MECA.

11. The method of claim 1, wherein said $A_3AR$ ligand is an $A_3AR$ allosteric enhancer.

12. The method of claim 11, wherein said $A_3AR$ allosteric enhancer is an imidazoquinoline derivative selected from the group consisting of:
N-(3,4-Dichloro-phenyl)-2-cyclopentyl-1H-imidazo[4,5-c]quinolin-4-amine;
N-(3,4-Dichloro-phenyl)-2-cycloheptyl-1H-imidazo[4,5-c]quinolin-4-amine;
N-(3,4-Dichloro-phenyl)-2-cyclobutyl-1H-imidazo[4,5-c]quinolin-4-amine; and
N-(3,4-Dichloro-phenyl)-2-cyclohexyl-1H-imidazo[4,5-c]quinolin-4-amine.

13. The method of claim 12, wherein said imidazoquinoline derivative is N-(3,4-Dichloro-phenyl)-2-cyclohexyl-1H-imidazo[4,5-c]quinolin-4-amine.

14. The method of claim 1, for treating a condition selected from the group consisting of erectile dysfunction, premature ejaculation, ejaculatory incompetence, retarded ejaculation, inhibited sexual desire, hypoactive sexual desire disorder, sexual aversion disorder, sexual arousal disorders, orgasm disorder and sexual pain disorder.

15. The method of claim 5, wherein said $A_3AR$ agonist is IB-MECA.

16. The method of claim 15, for inducing or improving sexual desire or erection.

17. The method of claim 13, for inducing or improving sexual desire or erection.

* * * * *